United States Patent [19]
Kanerva et al.

[11] Patent Number: 5,514,589
[45] Date of Patent: May 7, 1996

[54] CHIRAL RESOLUTION OF AN INTERMEDIATE IN DILTIAZEM SYNTHESIS USING LIPASE PS IMMOBILIZED WITH SUCROSE

[75] Inventors: Liisa Kanerva, Littoinen; Oskari Sundholm, Turku; Pekka Kairisalo, Helsinki; Martti Hytönen, Espoo, all of Finland

[73] Assignee: Orion-yhtymä Oy Fermion, Espoo, Finland

[21] Appl. No.: 215,529

[22] Filed: Mar. 22, 1994

[30] Foreign Application Priority Data

Mar. 24, 1993 [FI] Finland .................................. 931298

[51] Int. Cl.⁶ ...................................... C12P 41/00
[52] U.S. Cl. ............................ 435/280; 435/135
[58] Field of Search ..................... 435/280, 135

[56] References Cited

U.S. PATENT DOCUMENTS

| | | | |
|---|---|---|---|
| 4,552,694 | 11/1985 | Igarashi et al. | 260/239.3 B |
| 4,908,469 | 3/1990 | Martin | 560/17 |
| 5,097,059 | 3/1992 | Giordano et al. | 560/17 |

FOREIGN PATENT DOCUMENTS

| | | |
|---|---|---|
| 0342904 | 11/1989 | European Pat. Off. . |
| 0353538 | 2/1990 | European Pat. Off. . |
| 0464895 | 1/1992 | European Pat. Off. . |
| 0498706 | 8/1992 | European Pat. Off. . |
| 3337176 | 4/1984 | Germany . |
| 2-190195 | 7/1990 | Japan . |

OTHER PUBLICATIONS

Parida S et al, J. Am. Chem. Soc. 113:2253–59 (1991).
Okumura S et al, BBA 575:156–165 (1979).
Hills M J et al, BBA 1042:237–240 (1990).
Kanerua L T et al, J. Chem Soc, Perkin Trans 1:2407–2410, 1:1385–1389 (1993).
Wang Y–F et al, J. Am Chem. Soc. 110:7200–7205 (1988).
Kirchner G et al, J. Am Chem Soc 107:7072–7076 (1985).
Chem. Pharm. Bull. 37(10) 2876–2878 (1989), vol. 37, No. 10, "Enzymatic Hydrolysis in Organic Solvents for Kinetic Resolution of Water–Insoluble α–Acyloxy Esters with Immobilized Lipases", Hiroyuki Akita et al.
J. Org, Chem. 1988, vol. 53, No. 23, pp. 5531–5534, "Anhydrides as Acylating Agents in Lipase–Catalyzed Stereoselective Esterification of Racemic Alcohols", Daniele Bianchi et al.
Pure & Appl. Chem, vol. 64, No. 8, pp. 1157–1163, 1992, "Mechanistic Enzymology in Non–Aqueous Media", Alan J. Russell et al.

*Primary Examiner*—Marian C. Knode
*Assistant Examiner*—S. Saucier
*Attorney, Agent, or Firm*—Burns, Doane, Swecker & Mathis

[57] ABSTRACT

An enzymatic method for the preparation of (2S,3S)-threo-alkyl-2-hydroxy-3-(4-methoxyphenyl)-3-(2-X-phenylthio)propionate, where X=$NO_2$, $NH_2$, $NHCOCH_3$, $NHCOCF_3$, $NHCO_2CH_3$, $NHCO_2C(CH_3)_3$ or NHCHO and R is an alkyl group, e.g., $CH_3$, or $CH_2CH_3$ in an essentially anhydrous organic solvent is described. In this method a lipase which stereospecifically acylates the (2R,3R)-enantiomer of the racemic mixture is used. After enzymatic reaction, the (2S,3S)-enantiomer and the acylated (2R,3R)-compound are separated, e.g., by flash-chromatography or by fraction crystallization of the (2S,3S)-compound from the reaction mixture.

6 Claims, No Drawings

CHIRAL RESOLUTION OF AN INTERMEDIATE IN DILTIAZEM SYNTHESIS USING LIPASE PS IMMOBILIZED WITH SUCROSE

The object of this invention is a new method for the manufacture of optically pure (2S,3S)- and (2R,3R)-threo-alkyl-2-hydroxy-3-(4-methoxyphenyl)-3-(2-X-phenylthio)-propionates 1 ($R_1=CH_3$, $CH_2CH_3$ etc.) or for the manufacture of the corresponding acylated compounds 2. These compounds can be used as valuable intermediates in the synthesis of diltiazem 3. The absolute configuration of diltiazem is (2S,3S). In the clinical use diltiazem is one of the most promising calcium channel inhibitors.

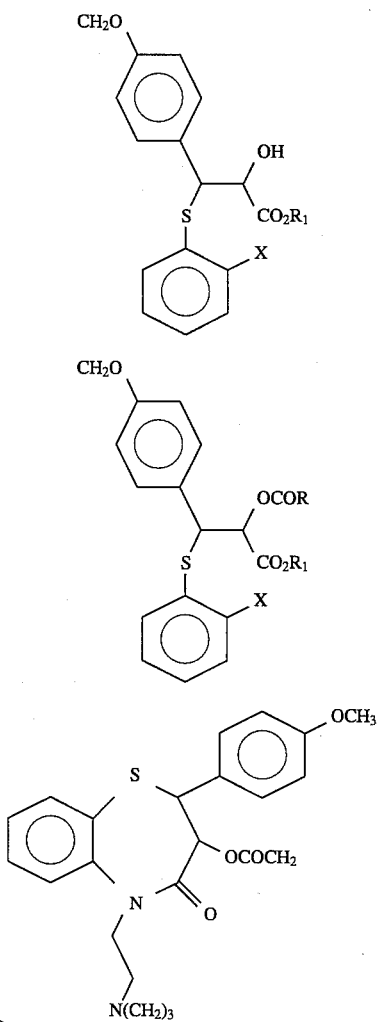

a: X = $NO_2$
b: X = $NH_2$
c: X = $NHCOCH_3$
d: X = $NHCOCF_3$
e: X = $NHCO_2CH_3$
f: X = $NHCO_2C(CH_2)_3$
g: X = NHCHO

The separation of (±)-2-hydroxy-3-(4-methoxyphenyl)-3-(2-aminophenylthio)propionic acid and propionates is described in the patent publications DE 3,337,176 and U.S. Pat. No. 4,908,469, and the separation of the corresponding enantiomers of (2-nitrophenylthio)propionic acid based on the formation of the diastereomeric salts with optically active aminoacids (L-lysine) or tartaric acid is described in the publication *Chem. Pharm. Bull.* 37 (1989) 3204–3208.

So far the only biocatalytical method for the manufacture of (2S,3S)-threo-alkyl-2-hydroxy-3-(4-methoxyphenyl)-3-(2-X-phenylthio)propionates describes the hydrolysis of the racemic threo-methyl-2-acyloxy-3-(4-methoxyphenyl)-3-(2-nitrophenylthio)propionate 2a catalyzed by lipase [*Chem. Pharm. Bull* 37 (1989) 2876-2878]. The enzymatic hydrolysis proceeds slowly because the compounds of types 1 and 2 are dissolved poorly in water. This is why the reactions have to be performed in an organic solvent, which is saturated with water. Additionally, the reaction is based on the kinetic control. Thus the yield of the optically active product remains low, if its highest possible optical purity is intended to be reached.

The object of this invention is the resolution of the racemic threo-alkyl-2-hydroxy-3-(4-methoxyphenyl)-3-(2-X-phenylthio)propionates 1 with a simple enzymatic method, which is based on a biocatalytic, practically almost enantiospecific acylation reaction of the secondary hydroxyl group in position 2 of compound 1 in anhydrous organic solvents. Different organic solvents can be used as solvent. Because the proteins as enzymes do not dissolve in organic solvents, it must specifically be taken care that the substrates and products dissolve in the chosen solvent. The advantage of the method described is the stability of the compound 1 with regard to the subsequent reactions. The yields of the reactions are good under the mild conditions. It also is advantageous that the described biocatalytic resolution is based on the selective reaction of the "wrong" enantiomer of the racemate with the achiral substrate and not on the formation of diastereomers. The chemical resolution similar to the formation of diastereomers requires the availability of an optically pure compound (L-lysine, for example), dismounting of the diastereomer and isolation of the liberated L-lysine, for example, and recycling of it from one resolution to another. In the reaction the unacylated (2S,3S)-enantiomer can be used for the manufacture of (2S,3S)-cis-diltiazem using the method described later.

As biocatalysts different commercial lipases were tested either as such or immobilized on solid supports (Celite and Chromosorb). Of the lipases tested *Mucor miehei* (Biocatalysts), *Candida lypolytica* (Biocatalysts), *Candida cylindracea* (Sigma), *Candida cylindracea* (AY 30, Amano), *Aspergillus. niger* (AP-6, Amano) and *Pseudomonas cepacia* (lipase PS, Amano), the lipase PS of Amano suits best for the purpose. In most cases it acts practically enantiospecifically, i.e. the reaction stops at 50% conversion and the products of the resolution (the unreacted enantiomer of the racemic mixture (2S,3S)-1 and the reaction product (2R, 3R)-2) can be isolated as optically pure substances with almost 100% yields. The activity of the immobilized lipase PS is multiple when compared to the activity of an untreated enzyme and the activity of the immobilized enzyme lasts longer in reuse.

It is characteristic to the method according to this invention that the enantiomer of the racemic compound according to the formula 1,

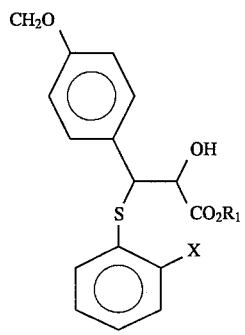

where X is —NO$_2$, —NH$_2$, —NHCOCH$_3$, —NHCOCF$_3$, —NHCO$_2$CH$_3$, —NHCO$_2$C(CH$_3$)$_3$ or —NHCHO and R$_1$ is —CH$_3$, —CH$_2$CH$_3$ etc., is allowed to react with a suitable acylating reagent in the presence of an untreated commercial enzyme or in the presence of an enzyme immobilized on a solid support in an organic solvent at the temperature of 20°–60 °C., when the acylated (2R,3R)-threo-alkyl-2-acetoxy-3-(4-methoxyphenyl)- 3-(2-X-phenylthio)propionate according to the formula 2 is obtained,

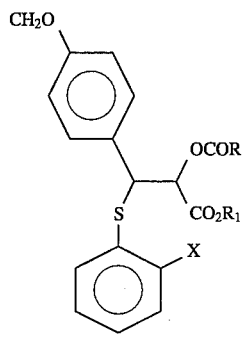

which is separated from the unreacted enantiomer (2S,3S)-1 chromatographically or using fraction crystallization from diethyl ether or from toluene.

The valuable drug substance diltiazem is obtained from the enantiomer (2S,3S)-1 by lactonizing the (2S,3S)-acid 4 after removing the protective groups (and reducing the nitro group, if X=NO$_2$).

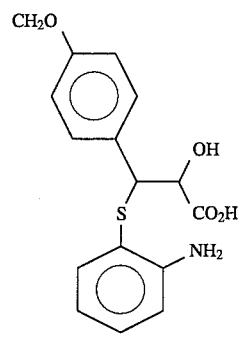

The aminoalkylation of lactame 5a is performed by using, for example, the mixture of toluene and N-methyl-pyrrolidin-2-one as solvent and potassium carbonate as base. The thus obtained aminoalkylation intermediate 5b is acylated with acetic anhydride, diltiazem 3 obtained is crystallized as its hydrochloride from ethanol.

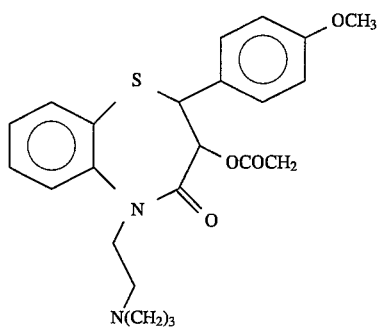

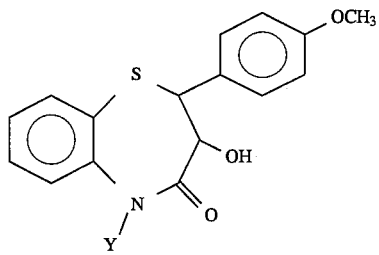

5a: Y = H
5b: Y = CH$_2$CH$_3$N(CH$_3$)$_2$

By using the method according to this invention the stereochemically pure compounds (2S,3S)-1 can be manufactured by applying the specificity of lipase when acylating the corresponding (2R,3R)-enantiomers in organic solvents. In the case of compound 1a the NO$_2$-group in position 2 in the thiophenol ring has to be reduced to NH$_2$-group for the synthesis of diltiazem. In the case of compound 1b there always occurs some acylation of the NH$_2$-group of the thiophenol ring un-enzymatically together with the enzymatic acylation. For that reason the final result is more unambiguous from the point of view of the quality of the product, if the mentioned NH$_2$-group is protected before the resolution with a suitable protection group. The protection of the amino group (manufacturing of compounds 1c–g) and the removal of the protection group after the resolution are performed using known methods.

According to the method of this invention any acylation reagent can be used, which is effective enough to acylate a sterically hindered alcohol 1 so that the reaction is completed within a reasonable time. It also is required that the equilibrium of the transesterification reaction favours the products as perfectly as possible because of the acylation reagent. Acid anhydrides, oxime esters, vinyl esters and activated esters, like 2,2,2-trifluoroethylacetate, are suitable acylation reagents. Some acylation reagents, like vinyl esters, can also be used as solvents. Other suitable solvents are especially diethylether and toluene, because the unreacted (2S,3S)-1 can thus be isolated after the concentration by fraction crystallization, when the enzyme has first been removed by filtration from the reaction mixture.

The invention is illustrated with following examples:

EXAMPLE 1

The specificity of Lipase PS and acylation of the racemic alcohol 1a–g
Method A 1 ml of the organic solvent, which is 0.05M with respect to one of the racemic alcohols 1a–g (R$_1$=CH$_3$ or CH$_2$CH$_3$) and 0.2M with respect to the vinyl- or acetoneoxime-acetate or acetic acid—or butyric anhydride, is added to the reaction vessel, which contains certain amount of commercially available lipase PS. The assay of the enzyme is presented in table 1. The reaction mixture is shaken effectively in a shaker at a temperature presented in the table. The proceeding of the reaction is followed by sampling the reaction mixture at suitable intervals, the enzyme is removed by filtering and then the sample is injected to the liquid chromatograph (column: C-18, eluent: MeOH/H$_2$O 70/30). The reaction stops at approx. 50% conversion. The excess of the unreacted (2S,3S)-enantiomer is determined by a HPLC method (column: chiralcel OG; eluent: hexane/isopropylalcohol 70/30) directly from the sample taken from the reaction mixture; in the case of compounds 1a, b and c the enantiomers do not separate perfectly under the HPLC conditions. This is why the e.e. values have been determined also in the presence of Eu(hfc)$_3$ using $^1$H NMR spectroscopy.

Method B

The used enzyme is immobilized on a solid support before using. For that reason 0.4 g of lipase PS is dissolved on icebatch in 15 ml of 20 mM of TRIS.HCl-buffer (pH 8.0). 240 mg of saccarose and 4 g of the support substance (Celite (Aldrich) or Chromosorb 101 (80–100 mesh, Sigma)) are added into that. The mixture is agitated for 10 –15 minutes. The enzyme preparation is allowed to dry on glass at room temperature.

The acylation of compounds 1a–g (R$_1$=CH$_3$) with vinyl acetate is performed as directed in method A except that such an amount of the enzyme preparation is weighed, that the amount of the lipase PS contained corresponds to the amounts given in table 1.

Results from methods A and B are presented in Table 1.

EXAMPLE 2

Manufacture of (2S,3S)-1a and (2R,3R)-2a 1.1 g (0.0030 mol) of racemic compound 1a (R$_1$=CH$_3$) and 0.80 ml (0.0085 mol) of acetic anhydride dissolved in 60 ml of tetrahydrofuran is added to the reaction vessel, which contains 6 g of enzyme (lipase PS). The reaction mixture is shaken at room temperature for two days, after which the reaction has stopped. The enzyme is separated by filtering and tetrahydrofuran is evaporated off. The residue which is dissolved in dichloromethane is washed with saturated NaHCO$_3$ solution and water. (2S,3S)-1a and (2R,3R)-2a (R=CH$_3$) are separated flash-chromatographically using the mixture of CH$_2$Cl$_2$/hexane/AcOEt (63/31/6) as an eluent. As a result, 0.56 g (0.0015 mol) of unreacted starting material 1a, which is an optically pure product according to the HPLC method in the example 1, and 0.63 g (0.0015 mol) of compound 2a (R=CH$_3$) are obtained. Both compounds are optically pure (e.e. >>95%) also by $^1$H NMR spectroscopic determination (1a, Eu(hfc)$_3$:CO$_2$Me, δ=3.84 and 3.94 used as a shifting reagent).

In order to determine the absolute configuration of the above prepared optically pure compound 1a it is hydrolyzed to the corresponding acid. 0.39 g of the above separated 1a is dissolved in 15 ml of a mixture of methanol and NaOH-solution (0.5M) 2/1. When the hydrolysis is completed the acid formed is precipitated by rendering the reaction mixture acidic with hydrochloric acid. The melting point of the resulting acid is 113°–114° C. and [α]$_D^{25}$=+112° (c 1, CHCl$_3$). The corresponding literature values for the (2 S, 3 S)-enantiomer of the acid are: the melting point 111° C. and

TABLE 1

| —X (R$_1$ = CH$_3$) | Solvent | Acylation reagent | Amano PS g/l | Time/d | Conversion/% | e.e.$^d$/% (2S,3S) |
|---|---|---|---|---|---|---|
| —NO$_2$ | THF (22° C.) | (CH$_3$CO)$_2$O | 100 | 2 | 50 | >>95 |
| —NO$_2$ | THF (22° C.) | (PrCO)$_2$O | 100 | 4 | 50 | >>95 |
| —NO$_2$ | THF (22° C.) | CH$_3$CO$_2$CH=CH$_2$ | 100 | 7 | 48 | >>95 |
| —NH$_2$ | Et$_2$O (22° C.) | CH$_3$CO$_2$CH=CH$_2$ | 25 | 3 | 50 | — |
| —NH$_2$ | Et$_2$O (20° C.) | CH$_3$CO$_2$—N=C(CH$_3$)$_2$ | 25 | 2 | 46 | — |
| —NH$_2$$^a$ | Et$_2$O (22° C.) | CH$_3$CO$_2$—N=C(CH$_3$)$_2$ | 5 | 2 | 51 | >>95 |
| —NH$_2$$^a$ | Et$_2$O (22° C.) | CH$_3$CO$_2$C(CH$_3$)=CH$_2$ | 5 | 2 | 50 | — |
| —NHCO$_2$CH$_3$ | Et$_2$O (22° C.) | CH$_3$CO$_2$CH=CH$_2$ | 5 | 2 | 50 | >>95 |
| —NHCO$_2$CH$_3$ | Et$_2$O (44° C.) | CH$_3$CO$_2$CH=CH$_2$ | 5 | 1 | 50 | >>95 |
| —NHCO$_2$CH$_3$ | CH$_3$CO$_2$CH=CH$_2$ (44° C.) | CH$_3$CO$_2$CH=CH$_2$ | 12.5 | 2 | 49 | 95 |
| —NHCO$_2$CH$_3$ | CH$_3$CO$_2$CH=CH$_2$/ Et$_2$O (1/1) (22° C.) | CH$_3$CO$_2$CH=CH$_2$ | 12.5 | 2 | 51 | 98 |
| —NHCO$_2$CH$_3$$^a$ | Et$_2$O (22° C.) | CH$_3$CO$_2$CH=CH$_2$ | 5 | 1 | 50 | >>95 |
| —NHCO$_2$CH$_3$$^b$ | Et$_2$O (44° C.) | CH$_3$CO$_2$CH=CH$_2$ | 2 | 1 | 50 | >>95 |
| —NHCO$_2$CH$_3$ | toluene (53° C.) | CH$_3$CO$_2$CH=CH$_2$ | 5 | 3 | 50 | >>95 |
| —NHCO$_2$CH$_3$$^c$ | Et$_2$O (22° C.) | CH$_3$CO$_2$CH=CH$_2$ | 100 | 1 | 50 | >>95 |
| —NHCO$_2$CH$_3$$^c$ | i-Pr$_2$O (44° C.) | CH$_3$CO$_2$CH=CH$_2$ | 100 | 1 | 49 | >>95 |
| —NHCO$_2$CH$_3$$^c$ | toluene (44° C.) | CH$_3$CO$_2$CH=CH$_2$ | 100 | 4 | 51 | >>95 |
| —NHCO$_2$C(CH$_3$)$_3$ | no reaction in described conditions | | | | | |
| —NHCOCH$_3$ | Et$_2$O (44° C.) | CH$_3$CO$_2$CH=CH$_2$ | 5 | 2 | 50 | >>95 |
| —NHCOCH$_3$ | CH$_3$CO$_2$CH=CH$_2$ (44° C.) | CH$_3$CO$_2$CH=CH$_2$ | 50 | 2 | 49 | — |
| —NHCOCH$_3$ | toluene (53° C.) | CH$_3$CO$_2$CH=CH$_2$ | 12.5 | 3 | 50 | >>95 |
| —NHCOCH$_3$$^a$ | Et$_2$O (44° C.) | CH$_3$CO$_2$CH=CH$_2$ | 2 | 1 | 46 | — |
| —NHCOCH$_3$$^b$ | Et$_2$O (44° C.) | CH$_3$CO$_2$CH=CH$_2$ | 2 | 1 | 52 | >>95 |
| —NHCOCF$_3$ | Et$_2$O (44° C.) | CH$_3$CO$_2$CH=CH$_2$ | 12.5 | 4 | 50 | >>95 |
| —NHCHO | CH$_3$CO$_2$CH=CH$_2$ | CH$_3$CO$_2$CH=CH$_2$ | 25 | 2 | 50 | — |

$^a$The enzyme is immobilized on chromosorb;
$^b$the enzyme is immobilized on celite;
$^c$R$_1$= CH$_2$CH$_3$;
$^d$e.e. >>95%, only one enantiomer to be detected $[\alpha]_D^{25}$=+121° (c 1, CHCl$_3$). [Senuma et al Chem. Pharm. Bull. 37 (1989) 3204].

EXAMPLE 3

Resolution of 1b

The enzyme is immobilized on Celite as described in example 1. 1.33 g (0.0040 mol) of the compound 1b (R$_1$=CH$_3$) and 0.92 ml (0.0080 mol) of acetoneoxime acetate dissolved in 40 ml of diethylether are added to the reaction vessel, which contains 1.25 g of the enzyme immobilized on Celite (0.2 g of lipase PS). The reaction is stopped after two days at 52% conversion. The enzyme is separated by filtering and the unreacted starting material 1b and the reaction product 2b (R=CH$_3$) are separated flash-chromatographically using the mixture of CH$_2$Cl$_2$/toluene/AcOEt (1/1/1) as an eluent. As a result 0.59 g (0 0018 mol) of white crystals of 1b, with $[\alpha]_D^{20}$=+294° (c 0.5,MeOH) and melting point 107°–109° C., are obtained. According to the specific optical rotation the compound is pure (2S,3S)-1b (in U.S. Pat. No. 4,908,469 the specific optical rotation at 22° C. temperature is +294° (c 0.5, MeOH) and the melting point 108°–109° C.). This reaction also results 0.68 g (0.0018 mol) of yellowish, amorphous compound (2R,3R)-2b (R=CH$_3$), $[\alpha]_D^{20}$=−258° (c 0.5, MeOH).

EXAMPLE 4

Resolution of 1c and manufacturing of (2S,3S)-1b and (2R,3R)-1b 6.0 g (0.016 mol) of the racemic compound 1c (R$_1$=CH$_3$) and 5.5 g (0.064 mol) of vinylacetate dissolved in 320 ml of diethylether is added to the reaction vessel, which contains 1.6 g of enzyme (lipase PS). The reaction mixture is shaken or mixed at reaction temperature (44° C.), until the reaction stops at 50% conversion (48 h). The proceeding of the reaction is followed using HPLC method (column: C-18; eluent: MeOH/H$_2$O 70/30). The enzyme is filtered and washed with diethylether, after which the enzyme can be reused. The ether solutions are combined and concentrated. (2S,3S)-1c crystallizes from the reaction mixture at −4° C. The crude product is recrystallized from diisopropylether, when 2.61 g (0.0070 mol, 87% of the theoretical yield) of white crystals, $[\alpha]_D^{25}$=+159° (c 1, CH$_2$Cl$_2$) and melting point 128°– 129° C. are obtained. Using flash chromatography the yield of (2S,3S)-1c is 50%, i.e. 100% of the theoretical yield of the resolution.

From the remaining reaction mixture 3.41 g (0.0080 mol, 100% of the theoretical yield) of the acetylated reaction product (2R,3R)-2c is separated using toluene/AcOEt/CH$_2$Cl$_2$ (1/1/1) as an eluent. The product is a yellowish oil, $[\alpha]_D^{25}$=−175° (c 1, CH$_2$Cl$_2$).

0.5 g (0.0013 mol) of optically pure (+)-(2S,3S)-1c is refluxed for 18 h in methanol (30 ml) in the presence of sulfuric acid (0.0052 mol). The reaction mixture is neutralized with sodium hydrogen carbonate and the methanol is evaporated off. The product is recrystallized from diethylether. 0.42 g (0.0013 mol, 98%) of (2S,3S)-1b, $[\alpha]_D^{20}$=+296° (c 0.5,MeOH) and melting point 108°– 110° C., is obtained as a product. In U.S. Pat. No. 4,908,469 the specific optical rotation of the same ester is stated 294° (c 0.5, MeOH) at 22° C. When refluxing correspondingly 1.1 g (0.0026 mol) of (−)-(2R,3R)-2c (R=CH$_3$) in methanol (50 ml), 0.811 g (0.0024 mol, 94%) of the compound (2R,3R)-1b, $[\alpha]_D^{20}$=−306° (c 0.5,MeOH ) and melting point 108°–109° C., as obtained. Based on the specific optical rotation, the resolution products are optically pure.

EXAMPLE 5

Manufacturing of (2S,3S)-1e and (2R,3R)-2e

Method A. 4.0 g (0.0010 mol) of the racemic compound 1e (R$_1$=CH$_3$) and 3.5 g (0.0041 mol) of vinylacetate dissolved in 205 ml of diethylether are added to the reaction vessel, containing is 1.03 g of enzyme (lipase PS). The reaction mixture is agitated effectively by shaking at room temperature. It can be noticed using the liquid chromatography (column: C-18; eluent: MeOH/H$_2$O 80/20) that the reaction has been completed (at 50% conversion) in two days, when according to the HPLC determination (column: Chiralcel OG; eluent: hexane/isopropylalcohol 70/30) the unreacted enantiomer (2S,3S)-1e is optically pure (e.e. 100%). The enzyme is filtered off and washed for reuse. The obtained ether solutions are combined and concentrated and (2S,3S)-1e is allowed to crystallize at −4 ° C. temperature. The crude product is recrystallized from diisopropylether. The yield is 1.39 g (70% from the theoretical yield) of white crystals, $[\alpha]_D^{25}$=+207° (c 1, CH$_2$Cl$_2$) and melting point 119°–121° C. According to the HPLC determination the product was optically pure.

From the remaining reaction mixture 2.15 g (0,005 mol, 100%) of an oily product (2R,3R)-2e is separated flash-chromatographically using toluene/Et$_2$O (2/1) as an eluent. $[\alpha]_D^{25}$ of the product =−193° (c 1, CH$_2$Cl$_2$).

The effect of the reuse of the enzyme filtered from the reaction mixture in the reaction time of two days is presented in table 2. In each case the reaction proceeds to 50% conversion and (2S,3S)-1e is obtained optically pure when the reaction time is extended.

TABLE 2

| Times used | Conversion/% | e.e. (2S,3S)/% |
|---|---|---|
| 1 | 50 | >>95 |
| 2 | 41 | 94 |
| 3 | 40 | 80 |

Method B. The enzyme is immobilized on Celite, as described in example 1. 4.64 g (0.0119 mol) of the racemic compound 1e (R$_1$=CH$_3$) and 4.1 g (0.047 mol) of vinylacetate dissolved in 240 ml of diethylether is added to the reaction vessel, containing 5.51 g of the above prepared enzyme (lipase PS, 0.475 g) immobilized on Celite. The reaction stops to 50% conversion in one day. The work-up of the reaction mixture is similar to method A. The yield of (2S,3S)-1e is 1.90 g (82%) of white crystals, $[\alpha]_D^{25}$=+212° (c 1, CH$_2$Cl$_2$) and melting point 118°–119° C. The yield of (2R,3R)-2e (R=CH$_3$) is 2.46 g (93%), $[\alpha]_D^{25}$=−199° (c 1, CH$_2$Cl$_2$).

The effect of the reuse of the enzyme preparate filtered from the reaction mixture in the reaction time of one day is presented in table 3.

TABLE 3

| Times used | Conversion/% | e.e. (2S,3S)/% |
|---|---|---|
| 1 | 48 | 98 |
| 2 | 51 | >>95 |
| 3 | 50 | >>95 |

We claim:

1. A method for the preparation of (2S,3S)-threo-alkyl-2-hydroxy-3-(4-methoxyphenyl)-3-(2-X-phenylthio)propionates and (2R,3R)-threo-alkyl-2-acyloxy-3-(4-methoxypheny-1)-3-(2-X-phenyl-thio)propionates according to formulae 1 and 2, below:

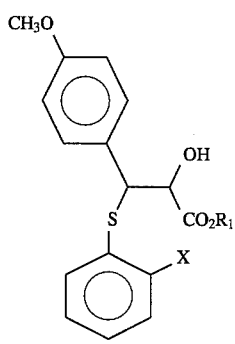

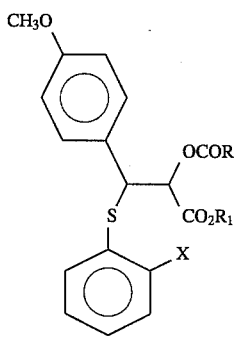

comprising reacting in anhydrous solvent or anhydrous solvents a racemic compound of formula 1, wherein X is selected from the group consisting of $NO_2$, $NH_2$, $NHCOCH_3$, $NHCOCF_3$, $NHCO_2CH_3$, and $NHCHO$ and $R_1$ is a methyl or ethyl group with an acylating reagent selected from the group consisting of acid anhydrides vinyl, esters and acetoneoxime acetate and a catalytically effective amount of Amano PS lipase which is immobilized in the presence of saccharose under conditions which provide for the acylation of the racemic compound of formula 1, and separating and recovering the resultant (2R,3R)-threo-alkyl-2-acyloxy-3-(4-methoxyphenyl)-3-(2-X-phenylthio)propionate of formula 2 from the (2S,3S)-threo-alkyl-2-hydroxy-3-(4-methoxyphenyl)-3-(2-X-phenylthio)propionate compound according to formula 1.

2. The method according to claim 1 wherein amino PS lipase is immoblized on celite or chromosorb.

3. The method according to claim 2 wherein the reaction temperature is 20°–60° C.

4. The method according to claim 2 wherein the compound (2S,3S)-1 is separated from the compound (2R,3R)-2 by fraction crystallization or chromatographically.

5. The method according to claim 1 wherein the reaction temperature is 20°–60° C.

6. The method according to claim 1 wherein the compound (2S,3S)-1 is separated from the compound (2R,3R)-2 by fraction crystallization or chromatographically.

* * * * *